(12) United States Patent  
Hendi

(10) Patent No.: US 6,313,300 B1  
(45) Date of Patent: Nov. 6, 2001

(54) OXIDATION PROCESS FOR PREPARING QUINACRIDONE PIGMENTS

(75) Inventor: Shivakumar Basalingappa Hendi, Newark, DE (US)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 09/638,190

(22) Filed: Aug. 14, 2000

Related U.S. Application Data

(60) Provisional application No. 60/152,706, filed on Sep. 7, 1999.

(51) Int. Cl.[7] ............................ C09B 48/00; C07D 471/04
(52) U.S. Cl. ............................ 546/49; 546/56; 546/57; 106/497; 106/495; 524/88; 524/90
(58) Field of Search ................... 546/49, 56, 57

(56) References Cited

U.S. PATENT DOCUMENTS

| | | | |
|---|---|---|---|
| 2,821,529 | 1/1958 | Struve | 260/279 |
| 2,969,366 | 1/1961 | Griswold et al. | 260/279 |
| 3,024,239 | 3/1962 | Caliezi | 260/279 |
| 3,148,075 | 9/1964 | Ehrich | 106/288 |
| 3,287,457 | 11/1966 | Higgins | 260/279 |
| 3,386,843 | 6/1968 | Jaffe et al. | 106/288 |
| 3,475,436 | 10/1969 | Cooper et al. | 260/279 |
| 3,610,510 | 10/1971 | Lowry | 229/8 |
| 3,738,988 | 6/1973 | Jackson | 260/279 |
| 4,310,359 | 1/1982 | Ehashi et al. | 106/288 |
| 4,371,643 | 2/1983 | Thomas | 524/88 |
| 4,692,189 | 9/1987 | Babler et al. | 106/308 |
| 4,783,540 | 11/1988 | Babler | 548/453 |
| 4,810,304 | 3/1989 | Jaffe et al. | 106/288 |
| 4,892,899 | 1/1990 | Jaffe et al. | 524/83 |
| 4,986,852 | 1/1991 | Dietz et al. | 106/498 |
| 5,093,497 | 3/1992 | Schutze et al. | 546/56 |
| 5,223,624 | 6/1993 | Babler et al. | 546/49 |
| 5,229,515 | 7/1993 | Pfenninger et al. | 546/49 |
| 5,286,863 | 2/1994 | Babler et al. | 546/56 |
| 5,457,203 | 10/1995 | Hendi et al. | 546/56 |
| 5,502,192 | 3/1996 | Ganci | 546/49 |
| 5,847,143 | * 12/1998 | Ganci | 546/56 |
| 5,856,488 | 1/1999 | Babler | 546/49 |

FOREIGN PATENT DOCUMENTS

| | | |
|---|---|---|
| 1 210 110 | 2/1966 | (DE) . |
| 3834748 | 4/1990 | (DE) . |
| 0321397 | 11/1988 | (EP) . |
| 0321919 | 12/1988 | (EP) . |

OTHER PUBLICATIONS

Abst. Page of JP 57 108 162.
Abst. Page of JP 54 135 821.
Abst. Page of JP 57119 958.
Abst. Page of DE 3 834 748.
Abst. Page of EP 0 362 690.
Abst. Page of JP 5814759.
Patent Abstracts of Japan vol. 007, No. 263 (c–196) 1983 of JP 58 147 459.
Chemical abst. of DE 1,210,110 64:16030F.

* cited by examiner

*Primary Examiner*—Evelyn Mei Huang
(74) *Attorney, Agent, or Firm*—David R. Crichton

(57) ABSTRACT

A process for preparing an unsubstituted or substituted quinacridone of the formula

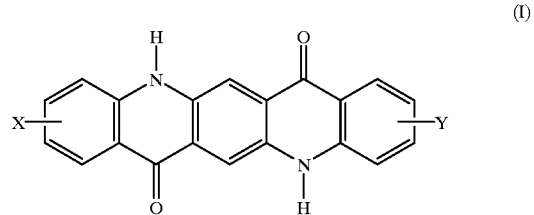

(I)

or a solid solution of quinacridones of the formula (I), wherein X and Y are independently 1 or 2 substituents selected from hydrogen, fluorine, chlorine, $C_1$–$C_3$alkyl, $C_1$–$C_3$alkoxy and COOR wherein R is hydrogen or $C_1$–$C_{10}$alkyl in which a salt of a corresponding 6,13-dihydroquinacridone of formula II

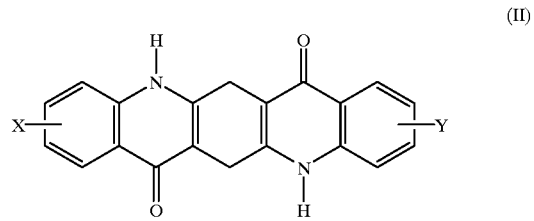

(II)

having the same substitutions as the desired quinacridone of formula I, or a mixture of corresponding 6,13-dihydroquinacridones of formula II, is oxidized with an oxygen containing gas in the presence of an aqueous base and a catalytically effective amount of an oxidation catalyst, characterized in that the oxidation is performed in the presence of an polyglycolic reaction medium of formula $$R_1\text{—O—}[(CH_2)_m\text{—}(CHR_1')_n\text{—O}]_x\text{—O—}R_1" \quad \text{(III)}.$$

20 Claims, No Drawings

OXIDATION PROCESS FOR PREPARING QUINACRIDONE PIGMENTS

This application claims the benefit of provisional application 60/152,706, filed on Sep. 7, 1999.

The present invention relates to a process for the preparation of quinacridone pigments by the catalyzed oxidation of the corresponding 6,13-dihydroquinacridone with air in a selected organic reaction medium.

Quinacridone pigments are known for their attractive red and magenta colors and for their outstanding fastness properties. It is well known in the art to prepare quinacridone pigments by oxidizing the correspondingly substituted 6,13-dihydroquinacridone. U.S. Pat. Nos. 2,821,529; 2,969,366; 3,148,075 and 3,287,457, for example, disclose the oxidation of a 6,13-dihydroquinacridone to the corresponding quinacridone in an alcoholic medium containing a base and a small amount of water using aromatic nitro compounds, e.g., the sodium salt of nitrobenzene sulfonic acid, or similar oxidizing agents.

U.S. Pat. No. 2,821,529 describes a process wherein various 6,13-dihydroquinacridones are oxidized to the corresponding quinacridone by heating a mixture containing the dihydroquinacridone and a mild oxidizing agent in an alkaline reaction medium. The medium is a mixture containing a major portion of an organic solvent, generally an alcohol, and a minor amount of water. The amount of water present in the reaction medium is small relative to the amount of the organic solvent.

The literature also describes processes for oxidizing a dihydroquinacridone to the corresponding quinacridone by utilizing molecular oxygen and a quinone compound as the oxidizing agent. Such a reaction is often referred to as an "air oxidation" because air is a preferred source of the molecular oxygen. In general, such oxidation processes are disclosed as taking place in an alkaline medium, usually an organic solvent containing a minor amount of water, in the presence of a quinone compound and molecular oxygen. The molecular oxygen is introduced to the reaction medium by bubbling an oxygen containing gas through the reaction medium or by blowing the oxygen containing gas above the surface thereof. Although the literature describes the quinone compound both as a catalyst and as an oxidizing agent, U.S. Pat. No. 3,024,239 discloses that the quinone is an oxidizing agent which is reduced to the corresponding leuco compound during the oxidation of the dihydroquinacridone. The molecular oxygen regenerates the quinone so that less than the stoichiometric amount of the quinone is required for the reaction to proceed to completion.

U.S. Pat. No. 3,475,436 discloses an air oxidation process wherein the reaction medium contains a major portion of tetramethylene sulfone and a relatively small amount of water. Similar processes which utilize an alkaline medium containing a major portion of other organic solvents, such as dimethylsulfoxide, dimethylacetamide, alkanediols, $C_1-C_3$ alcohols caprolactam and N-alkyl-2-pyrrolidone, usually in the presence of a relatively small amount of water, are also known in the art.

The air oxidation of dihydroquinacridones in an aqueous reaction medium and in the presence of a divalent metal ion or a quaternary ammonium salt is also known. For example, U.S. Pat. No. 3,738,988 discloses a process wherein an aqueous medium is utilized and teaches that the oxidation step should be carried out in the presence of divalent iron, cobalt or nickel ions in order to increase the effectiveness of the oxidation. JP 53/904334 discloses an oxidation media including $C_1-C_3$ alcohols and aqueous base, together with air. DE 3,834,748 and U.S. Pat. No. 5,093,497 describe the addition of a quaternary ammonium salt to the oxidation in both aqueous and organic reaction media.

U.S. Pat. No. 5,502,192 describes the conversion of the 6,13-dihydroquinacridone to the corresponding quinacridone in an aqueous medium via an air oxidation process in which the aqueous reaction medium also contains a relatively minor amount of a nonionic, polar organic material which forms a liquid, organic second-phase in the reaction mixture.

In many of the aforementioned processes, the reactants and resulting products are generally not in solution and consequently must be suspended during the oxidation reaction. The resulting pigments are filtered directly from the reaction mixture. The disadvantages encountered with these approaches include incomplete oxidation, long oxidation reaction cycles and particularly the crude nature of the isolated pigments which are relatively large in particle size. Because of the crude nature of the recovered pigment, additional conditioning steps are required to obtain a commercially acceptable strong transparent pigment.

Still other patents disclose the use of N-alkyl-2-pyrrolidone (JP 57/119958) or N-methyl-ε-caprolactam (JP 57/108162), or a mixture of polar solvents (JP 58/147459) together with base and preferably nitro compounds such as sodium m-nitrobenzene-sulfonate as the oxidation agent. Although air and oxygen are mentioned as potential oxidizing agents, the yield of quinacridones and substituted quinacridones obtained by such processes are not quantitative due to incomplete oxidation or concomitant over oxidation to quinacridonequinone. Furthermore, the use of solvent mixtures and aromatic nitro compounds requires expensive deposition of the organic reduction products which must be disposed of in an ecologically acceptable manner.

JP 54/135821 discloses the preparation of quinacridone pigments involving the oxidation of 6,13-dihydroquinacridone in dimethylsulfoxide in the presence of water, an alkali and an oxidizing agent such as sodium o-nitrobenzenesulfonate, sodium m-nitrobenzenesulfonate, sulfur powder, selenium, iodine or air, to obtain a quinacridone salt solution, which when diluted with a polar solvent or acid yields a finely divided product. Although this process produces quinacridones directly in pigmentary form, the use of air in such a process requires long reaction times and results in low yields of quinacridones as a consequence of the formation of quinacridonequinone and the presence of residual unoxidized 6,13-dihydroquinacridone. Furthermore, only unsubstituted quinacridones are described as being applicable to this method.

U.S. Pat. No. 5,286,863 describes a process for preparing quinacridone pigments in which 6,13-dihydroquinacridone or a derivative thereof is oxidized at an elevated temperature in the presence of a base, a dimethylsulfoxide medium and a quinone catalyst. This method is described as providing a direct synthesis of pigmentary grade quinacridone that does not require post synthesis conditioning, without the use of organic oxidizing agents or surfactants. U.S. Pat. No. 5,223, 624 describes the synthesis of a unique $\gamma_{III}$ form of quinacridone in which 6,13-dihydroquinacridone is oxidized in a dimethylsulfoxide medium.

Applicants have found that the direct oxidation of unsubstituted and/or substituted 6,13-dihydroquinacridones provides corresponding quinacridones in short reaction times and high yields when the oxidation is conducted in a selected organic reaction medium, most preferably a polyalkylene glycol medium, in the presence of an aqueous base, with air or another oxygen-containing gas mixture at a temperature below 100° C., catalyzed by a quinone or quinone derivative. In addition, the resulting solutions, upon subjection to hydrolysis or alcoholysis (drowning), optionally in the presence of an acid, provide quinacridones in a final pigmentary form that requires no post-synthesis particle size reduction procedures.

The use of a selected organic reaction medium allows the direct oxidation of substituted and/or unsubstituted 6,13-dihydroquinacridone to the corresponding quinacridone in an ecologically effective manner, i.e., without the use of organic oxidizing agents or surfactants, such that virtually no waste products are generated. The procedure also allows the introduction of particle growth inhibitors directly in to the reaction mixture whereby small particle size, transparent pigments can be obtained directly from synthesis without requiring mechanical size reduction (e.g., milling).

In addition, it has been unexpectedly found that the air oxidation of an unsubstituted dihydroquinacridone in a selected organic reaction medium, such as a polyalkylene glycol medium, results in an unsubstituted quinacridone, the polymorphic phase of which is dictated by the drowning conditions. Specifically, it has been found that in polyalkylene glycol oxidations, drowning in water provides (α quinacridone, drowning in methanol produces a β quinacridone (with varying levels of α phase contamination) and most unexpectedly, provides a $\gamma_I$ polytype quinacridone upon drowning in hot methanol.

Air oxidation of dihydroquinacridones to the corresponding quinacridone in a selected organic reaction medium is both economically attractive and environmentally friendly. The polyalkylene glycol oxidation route leads directly to pigmentary grade quinacridones requiring no particle size reducing milling or grinding operations. Further, polyalkylene glycol air oxidation of dihydroquinacridones to the corresponding quinacridone allows one to control the polymorphic state of the resulting pigment by simply altering the drowning conditions. As is clear, many benefits result from the use of the oxidation process of the instant invention.

Accordingly, the present invention relates to a process for preparing a quinacridone of formula I

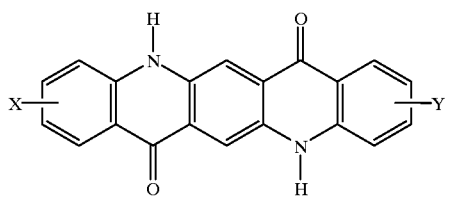

(I)

wherein X and Y are independently 1 or 2 substituents selected from the group consisting of H, F, Cl, $C_1$–$C_3$alkyl, $C_1$–$C_3$alkoxy and COOR, wherein R is H or $C_1$–$C_{10}$alkyl, by the oxidation of a salt of the corresponding 6,13-dihydroquinacridone of formula II

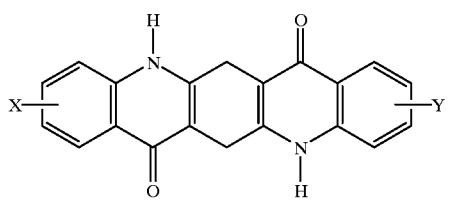

(II)

which comprises an oxidation step wherein the 6,13-dihydroquinacridone salt is oxidized with air or another oxygen containing gas mixture in a reaction medium containing an oxidative effective amount of a compound represented by formula (III)

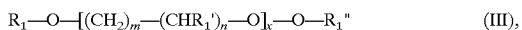

$R_1\text{—O—}[(CH_2)_m\text{—}(CHR_1')_n\text{—O}]_x\text{—O—}R_1''$ (III), wherein $R_1$, $R_1'$, $R_1''$ are, independently of one another, hydrogen or $C_1$–$C_4$alkyl, or $R_1$ and $R_1''$ are together $C_2$–$C_4$alkylene, m and n=1 to 4, and x=3 to 1000, in the presence of an aqueous base and a catalyst. Linear compounds, however, are highly preferred to cyclic compounds for economical, environmental and practical reasons. Polyethylene glycol and derivatives thereof are most preferred.

More preferably the dihydroquinacridone salt or mixtures thereof are oxidized with air or another oxygen containing gas mixture in a polyalkylene glycol medium in the presence of an aqueous base and a catalyst.

The process of this invention is particularly suitable for the preparation of quinacridone, 2,9-dichloroquinacridone, 2,9-difluoroquinacridone, 4,11-dichloroquinacridone, 4,11-difluoroquinacridone, 2,9-dicarboxyquinacridone, 3,10-dichloroquinacridone, 2,9-dimethylquinacridone and 2,9-dimethoxyquinacridone, in addition to any other substituted quinacridones that can be prepared from the corresponding 6,13-dihydroquinacridones by means of the described process.

Additionally, the process of this invention is also suitable for the preparation of quinacridone solid solutions such as, for example, those described in U.S. Pat. Nos. 3,610,510, 4,783,540 or 4,810,304. Thus, mixtures of unsubstituted dihydroquinacridone and/or differently substituted 6,13-dihydroquinacridones are either co-reacted according to the process of this invention or the pigment solutions of separately oxidized 6,13-dihydroquinacridones are mixed and the solid solution pigment is precipitated according to the present invention.

Polyalkylene glycol or mixtures thereof having a weight average molecular weight in the range of from about 200 to about 1000, preferably about 200 to 600, most preferably 300 to 400, are especially suitable for use as the reaction medium of the claimed process. Using anthraquinone-2-sulfonic acid as the catalyst, air oxidation of dihydroquinacridones in both PEG 400 (polyethylene glycol with a molecular weight of 400) and PEG 300 was found to result in a commercially important β polymorph of 2,9-dimethylquinacridone, whereas a mixed phase product is obtained using PEG 200. The polyalkylene glycol(s) suitable for use according to the invention are generally present in technical quality in an amount ranging from 40 to 2 times the weight of 6,13-dihydroquinacridone and/or its derivatives and preferably 25 to 3 times the weight thereof. Although more than 40 times the weight of polyalkylene glycol can be used to oxidize dihydroquinacridones with excellent conversion yields, it becomes impractical and uneconomical to use such high amounts of polyalkylene glycol. Surprisingly, it was found that the use of ethylene glycol failed to produce a fully oxidized product. Although not wishing to be bound by any theory, it is believed that the ether linkages in the polyglycols are needed and presumably act as crown ethers.

Bases which prove particularly suitable for this process are, for example, alkali metal hydroxides such as sodium hydroxide and potassium hydroxide. A suitable molar ratio of 6,13-dihydroquinacridone to base is about 1:3 to 1:39, preferably about 1:4 to 1:15. Preferably, the aqueous base used in the oxidation step of the present process is either 50% sodium hydroxide or 45% potassium hydroxide and is used in an amount of about 1.0 to 3.0 parts per part of dihydroquinacridone. More than 3.0 parts of base can also be used in these oxidations, however using more base, and hence more water, may cause the reaction to become heterogeneous. It is very important to keep the reaction mixture homogeneous; dihydroquinacridone in the form of a salt form and the resulting quinacridone in the form of a salt in solution.

The presence of water during the oxidation step is essential for base solubility in the selected organic reaction medium. It is preferable to add the base as an aqueous solution. For example, an aqueous solution containing 70–30 parts of an alkali hydroxide and 30–70 parts of water, for example commercially available 45% aqueous potassium hydroxide or an about 50% aqueous solution of sodium hydroxide, may be used in the oxidation procedures of the present invention. An aqueous solution containing 52–30 parts of sodium hydroxide and 30–48 parts of water is most preferably used.

Oxidizing agents include oxygen-containing gas mixtures, for example, oxygen/nitrogen or oxygen/argon mixtures with at least 2% oxygen. Air is preferably used. The oxygen-containing gas mixture is introduced below or above the surface of the reaction mixture. The oxidation reaction is conducted at temperatures below 150° C., preferably at 50–100° C. and most preferably at 70–90° C. Additionally, the oxidation reaction can be conducted under pressure.

The presence of catalytic amounts of a quinone and/or derivatives thereof during the oxidation reaction results in obtaining high yields of the quinacridone in shorter reaction times. The presence of the catalyst and the use of the indicated reaction temperatures and other variables result in quinacridone products which are substantially devoid of over-oxidation products such as quinacridonequinones which adversely affect the intensity of the resulting quinacridone product.

Particularly suitable quinone catalysts are, for example, anthraquinone and its derivatives such as mono and/or dichloroanthraquinone and most preferably anthraquinone-2-sulfonic acid and/or 2,6-disulfonic acid derivatives. The quinone catalyst is present in an amount ranging from 0.005 to 0.25 times the weight of 6,13-dihydroquinacridone or derivative, and most preferably 0.01 to 0.15 times the weight. Again, higher levels of catalyst do not hurt the oxidation reaction but are not required.

After the oxidation is completed, the generated salt of the quinacridone is completely dissolved in the organic reaction medium. Depending on the amount of dihydroquinacridone used, the reaction mixture can be fluid enough to process easily. Where higher dihydroquinacridone levels are used, the reaction mixtures tend to be viscous. In such cases it is possible to dilute the reaction mixture after oxidation with a suitable solvent. Preferred solvents are those that are miscible in the reaction mixture and will not initiate the precipitation of the pigment from the reaction mixture. For example, it is possible to use requisite amounts of water and/or methanol for this purpose. In diluting the reaction mixtures with excess water and/or methanol, there is a possibility that the quinacridone pigment may start precipitating.

Several precipitation methods are available for precipitating the quinacridone and/or its derivatives from the pigment salt solution. In a preferred procedure, the reaction mixture is drowned into an alcohol such as methanol, ethanol, n-propanol, iso-propanol, n-butanol or its isomers and/or water. As previously noted, it is an advantage of the present process that the polymorphic phase of unsubstituted and substituted quinacridones can be controlled by the selection of the drowning medium. For instance, drowning the oxidation reaction mixture of 6,13-dihydroquinacridone with the use of water results in an α phase unsubstituted quinacridone. Whereas the use of alcohols such as methanol provides a commercially important β phase 2,9-dimethylquinacridone after drowning the oxidation reaction mixture of the corresponding dihydroquinacridone. Surprisingly, the use of a hot (40° C. to 97° C.) alcohol, particularly refluxing methanol, leads to the formation of a desirable $\gamma_I$ polytype unsubstituted quinacridone.

In another applicable procedure, the quinacridone pigment is precipitated by adding an alcohol and/or water to the reaction mixture. Precipitation may also be initiated using mineral acids such as dilute hydrochloric-, phosphoric-, and sulfuric acids or organic acids such as $C_2$–$C_8$ mono-, di- or tri-carboxylic acids, for example acetic acid, optionally in conjunction with organic solvents; or by the direct introduction of hydrogen halide gas, for example hydrogen chloride, into the reaction mixture.

Depending on the selected precipitation conditions, a transparent, small particle size (<0.1 μm) or an opaque large particle size (>0.2 μm) pigment form can be obtained. As previously noted, the ability to directly obtain transparent, small particle size pigments without the need for mechanical size reduction operations is a decided benefit. Furthermore, it is possible to conduct the precipitation in such a manner that selected crystal modifications of all quinacridones can be obtained. Such polymorphic modifications are known and have been described, for example, in Chemical Reviews, 67, 1, 1–18 (1967). In general, more opaque pigments are generated when an alcohol is chosen as the precipitation medium and the resulting pigment suspension is stirred for 1 to 24 hours at atmospheric or higher pressures and temperatures of 20° C. or higher.

The particle size of the pigment is controlled by varying the time and the temperature of the treatment in the basic solvent mixture. A greater degree of particle size control, particularly for small particle size pigments, can be exercised by adding particle growth inhibitors such as sulfonic acid, phthalimidomethyl-, imidazolylmethyl-, pyrazolylmethyl-, N-(diakylaminoalkyl)sulfonic acid amide derivatives of the quinacridone. Such particle growth inhibitors may also act under certain conditions as crystal phase directors. Particle growth inhibitors, also known as antiflocculating agents, are well known and described, for example, in U.S. Pat. No. 3,386,843, 4,310,359, 4,692,189, EP 321397, EP 321919, and EP 362690.

The particle growth inhibitors are added in amounts ranging from 0.05 to 15%, preferably 1 to 8%, and most preferably 2 to 5% based on the corresponding pigment, either after but preferably, before the precipitation of the oxidized pigment. They can additionally serve to lessen or avoid flocculation, increase pigment dispersion stability and positively affect Theological characteristics.

When the ripening of the pigment crystals is complete, the pigment in its desired pigmentary form can be isolated by, for example, filtration or centrifugation, with the presscake being washed with water or an organic solvent, preferably methanol, followed by water and dried. Depending on the end use, it can be advantageous to add specific amounts of texture improving agents to the pigment. Suitable texture improving agents are, in particular, fatty acids of not less than 18 carbon atoms, for example stearic or behenic acid or the amides or metal salts thereof, preferably calcium or magnesium salts, as well as plasticizers, waxes, resin acids such as abietic acid or metal salts thereof, colophonium, alkyl phenols or aliphatic alcohols such as stearyl alcohol or vicinal diols such as dodecane-1,2-diol, and also modified colophonium/-maleate resins or fumaric acid/colophonium resins or polymeric dispersants. The texture improving agents are preferably added in amounts of 0.1 to 30%, by weight, most preferably 2 to 15% by weight, based on the final product.

The compositions of this invention are suitable for use as pigments for coloring high molecular weight organic materials. Examples of high molecular weight organic materials which may be colored or pigmented with the compositions of this invention are cellulose ethers and esters such as ethylcellulose, nitrocellulose, cellulose acetate, cellulose butyrate, natural resins or synthetic resins such as polymerization resins or condensation resins, for example aminoplasts, in particular urea/formaldehyde and melamine/formaldehyde resins, alkyd resins, acrylic resins, phenolic plastics, polycarbonates, polyolefins, polystyrene, polyvinyl chloride, polyamides, polyether, polyetherketone, polyurethanes, polyesters, rubber, casein, silicone and silicone resins, singly or in mixture.

The above high molecular weight compounds may be used singly or as mixtures in the form of plastics, melts or of spinning solutions, varnishes, paints or printing inks. Depending on the end use, it is advantageous to use the pigments as toners or in the form of preparations. The compositions of the invention are preferably employed in an amount of 0.1 to 30% by weight based on the high molecular organic material to be pigmented.

Pigmentation of high molecular weight organic compounds with the pigments of the invention is carried out, for example, by incorporating such pigments, optionally in the form of a masterbatch, into the substrates using roller mills, mixing or grinding machines. The pigmented material is then brought into the desired final form by methods which are known per se, for example, calendering, molding, extruding, coating, spinning, casting or by injection molding. It is often desirable to incorporate plasticizers into the high molecular weight compounds before processing in order to produce non-brittle moldings or to diminish their brittleness. Suitable plasticizers are, for example, esters of phosphoric acid, phthalic acid or sebacic acid. The plasticizers may be incorporated before or after working the composition into the polymers. To obtain different shades, it is also possible to add fillers or other chromophoric components such as white, colored or black pigments, in any amount, to the high molecular weight organic compounds, in addition to the compositions of this invention.

For pigmenting varnishes and printing inks, the high molecular weight organic materials and the pigments obtained according to the present invention, together with optional additives such as fillers, other pigments, siccatives or plasticizers, are finely dispersed or dissolved in a common organic solvent or mixture of solvents. The procedure may be such that the individual components or blends thereof are dispersed or dissolved in the solvent and subsequently all the components are mixed.

The following examples further illustrate the preferred embodiments of this invention. In these examples, all parts given are by weight unless otherwise noted.

EXAMPLE 1

To a one liter four necked round bottomed flask equipped with a stirrer, thermometer, a gas inlet tube and reflux condenser was added aqueous sodium hydroxide (80 g; 50%), 2,9-dimethyl-6,13-dihydroquinacridone crude (40.0 g; 0.117 moles), anthraquinone-2-sulfonic acid (4.0 g), 2-phthalimidomethylquinacridone (0.8 g) and polyethylene glycol 400 (360 g). Air was bubbled into the stirred mixture. The reaction mixture was heated with stirring and maintained at 90±2° C. for 3.0 hours. The deep violet-black reaction mixture was cooled to 25° C. To this mixture was added methanol (400 ml) with vigorous stirring.

Part A: One half of the above slurry was poured in to water (1200 ml). The precipitated product was filtered, washed with hot (60° C.) water until the pH of the filtrate was 7.0. The resulting pigment presscake was dried at in an oven overnight at 80° C. to yield 19.6 g of an attractive magenta colored pigment which analyzed for 96.9% 2,9-dimethylquinacridone; 0.1% 2,9-dimethyl-6,13-dihydroquinacridone and 0.8% 2,9-dimethylquinacridonequinone. The product showed an X-ray diffraction pattern of a β polymorph 2,9-dimethylquinacridone.

Part B: The other half of the above slurry was poured in to methanol (1200 ml). The precipitated product was filtered, washed with hot (60° C.) water until the pH of the filtrate was 7.0. The resulting pigment presscake was dried overnight in an oven at 80° C. to yield 19.4 g of a brilliant magenta colored pigment which analyzed for 98.6% 2,9-dimethylquinacridone; 0.1% 2,9-dimethyl-6,13-dihydroquinacridone and 0.1% 2,9-dimethylquinacridonequinone. The product showed an X-ray diffraction pattern of a β polymorph 2,9-dimethylquinacridone.

Pouring the oxidation slurry into methanol is found to result in a pigment with better crystallinity compared to a pigment formed by pouring the slurry into water. Also, the pigment obtained from drowning in methanol is coloristically more attractive.

EXAMPLE 2

To a one liter four necked round bottomed flask equipped with a stirrer, thermometer, a gas inlet tube and reflux condenser is added aqueous sodium hydroxide (80 g; 50%), 2,9-dimethyl-6,13-dihydroquinacridone crude (40.0 g; 0.117 moles), anthraquinone-2-sulfonic acid (4.0 g) and polyethylene glycol 400 (360 g). Air is bubbled into the stirred mixture. The reaction mixture is heated with stirring and maintained at 90±2° C. for 3.0 hours. The deep violet-black reaction mixture is cooled to 25° C. and to this mixture is added 2-phthalimidomethylquinacridone (0.8 g). After stirring for ¼ hour the reaction mixture is poured into methanol (1200 ml) with vigorous stirring. The precipitated product is filtered, washed with hot (60° C.) water until the pH of the filtrate is 7.0. The resulting pigment presscake is dried overnight in an oven at 80° C. to yield 39.6 g of an attractive magenta colored pigment which is similar to the pigment of Example 1.

The product shows an X-ray diffraction pattern of a β polymorph 2,9-dimethylquinacridone. As is shown, a growth inhibitor can be introduced after the oxidation is complete but before quenching the alkali metal salt of the quinacridone to provide a desired particle size pigment.

EXAMPLE 3

To a one liter four necked round bottomed flask equipped with a stirrer, thermometer, a gas inlet tube and reflux condenser was added aqueous sodium hydroxide (80 g; 50%), 6,13-dihydroquinacridone crude (39.2 g; 0.1248 moles), anthraquinone-2-sulfonic acid (4.0 g), polyethylene glycol 400 (360 g) and 2-phthalimidomethylquinacridone (0.8 g). Air was bubbled into the stirred mixture. The reaction mixture was heated with stirring and maintained at 90±2° C. for 3.0 hours. The deep violet-black reaction mixture was cooled to 25° C. To this mixture was added methanol (400 ml) with vigorous stirring.

Part A: One half of the above slurry was poured into water (900 ml). After ¼ hour of stirring the precipitated product was filtered, washed with hot (60° C.) water until the pH of the filtrate was 7.0. The resulting pigment presscake was dried overnight in an oven at 80° C. to yield 19.4 g of a deep red colored α quinacridone pigment (X-ray diffraction).

Part B: The other half of the above slurry was poured in to methanol (900 ml). After ¼ hour of stirring the precipitated product was filtered, washed with hot (60° C.) water until the pH of the filtrate was 7.0. The resulting pigment presscake was dried overnight in an oven at 80° C. to yield 19.4 g of a very dull-violet colored pigment which showed an X-ray diffraction of a mixture of α and β quinacridone.

EXAMPLE 4

To a one liter four necked round bottomed flask equipped with a stirrer, thermometer, a gas inlet tube and reflux condenser was added aqueous sodium hydroxide (80 g; 50%), 2,9-dichloro-6,13-dihydroquinacridone crude (39.2 g; 0.1024 moles), anthraquinone-2-sulfonic acid (4.0 g) 2-phthalimidomethylquinacridone (0.8 g) and polyethylene glycol 400 (360 g). Air was bubbled in to the stirred mixture. The reaction mixture was heated with stirring and maintained at 90±2° C. for 3.0 hours. The dark blue reaction mixture was cooled to 25° C. To this mixture was added methanol (400 ml) with vigorous stirring.

Part A: One half of the above slurry was poured into water (900 ml). After ¼ hour of stirring the precipitated product was filtered, washed with hot (60° C.) water until the pHl of the filtrate was 7.0. The resulting pigment presscake was dried overnight in an oven at 80° C. to yield 19.4 g of a deep magenta colored pigment which showed an X-ray diffraction of a γ polymorph of 2,9-dichloroquinacridone of an extremely small particle size.

Part B: The other half of the above slurry was poured into methanol (900 ml). After ¼ hour of stirring the precipitated product was filtered, washed with hot (60° C.) water until the pH of the filtrate was 7.0. The resulting pigment presscake was dried overnight in an oven at 80° C. to yield 19.4 g of a very small particle size y 2,9-dichloroquinacridone pigment with an attractive deep magenta color.

EXAMPLE 5

To a one liter four necked round bottomed flask equipped with a stirrer, thermometer, a gas inlet tube and reflux condenser was added aqueous sodium hydroxide (80 g; 50%), 2,9-dichloro-6,13-dihydroquinacridone crude (35.3 g; 0.0922 moles), 6,13-dihydroquinacridone crude (3.9 g; 0.0124 moles), anthraquinone-2-sulfonic acid (4.0 g), 2-phthalimidomethylquinacridone (0.8 g) and polyethylene glycol 400 (360 g). Air was bubbled into the stirred mixture. The reaction mixture was heated with stirring and maintained at 90±2° C. for 3.0 hours. The dark blue reaction mixture was cooled to 25° C. To this mixture was added methanol (400 ml) with vigorous stirring.

Part A: One half of the above slurry was poured in to water (900 ml). After ¼ hour of stirring the precipitated product was filtered, washed with hot (60° C.) water until the pH of the filtrate was 7.0. The resulting pigment presscake was dried overnight in an oven at 80° C. to yield 19.4 g of a deep magenta colored pigment with an X-ray diffraction of a very small particle size 90/10 solid solution of 2,9-dichloroquinacridone and unsubstituted quinacridone.

Part B: The other half of the above slurry was poured into methanol (900 ml). After ¼ hour of stirring the precipitated product was filtered, washed with hot (60° C.) water until the pH of the filtrate was 7.0. The resulting pigment presscake was dried overnight in an oven at 80° C. to yield 19.4 g of a very small particle size solid solution pigment of a 90/10 composition of 2,9-dichloroquinacridone and unsubstituted quinacridone. The pigment possessed a very attractive deep magenta color.

Polyethylene glycol surprisingly serves as an excellent solvent in the co-oxidation of a variety of substituted and/or unsubstituted dihydroquinacridones resulting in solid solution pigments. It is particularly surprising that the quinacridones generated by the co-oxidation of the dihydroquinacridones do not crystallize as separate entities. Hence, it is possible to perform step a) separately in a different reactor for each compound of formula (II), then to combine these reaction mixtures before precipitating in step b). This advantageously leads to more production flexibility, while similar results are obtained.

EXAMPLE 6

To a one liter four necked round bottomed flask equipped with a stirrer, thermometer, a gas inlet tube and reflux condenser was added aqueous sodium hydroxide (80 g; 50%), 2,9-dimethyl-6,13-dihydroquinacridone crude (40.0 g; 0.117 moles), anthraquinone-2-sulfonic acid (4.0 g) and polyethylene glycol 400 (360 g). Air was bubbled into the stirred mixture. The reaction mixture was heated with stirring and maintained at 90±2° C. for 3.0 hours. The dark purple reaction mixture was cooled to 25° C. To this mixture was added methanol (400 ml) with vigorous stirring.

Part A: One half of the above slurry was poured into water (900 ml). After ¼ hour of stirring the precipitated product was filtered, washed with hot (60° C.) water until the pH of the filtrate was 7.0. The resulting pigment presscake was dried overnight in an oven at 80° C. to yield 19.4 g of a deep magenta colored pigment which showed an X-ray diffraction pattern of a less crystalline β polymorph of 2,9-dimethylquinacridone of a very small particle size.

Part B: The other half of the above slurry was poured into methanol (900 ml). After ¼ hour of stirring the precipitated product was filtered, washed with hot (60° C.) water until the pH of the filtrate was 7.0. The resulting pigment presscake was dried overnight in an oven at 80° C. to yield 19.4 g of a very small particle size pigment with an attractive deep magenta color. The pigment showed an X-ray diffraction pattern of small particle size 2,9-dimethylquinacridone of better crystallinity compared to the pigment of Example 6, Part A.

EXAMPLE 7

To a one liter four necked round bottomed flask equipped with a stirrer, thermometer, a gas inlet tube and reflux condenser was added aqueous sodium hydroxide (80 g; 50%), 2,9-dimethyl-6,13-dihydroquinacridone crude (39.2 g; 0.1146 moles), anthraquinone-2-sulfonic acid (4.0 g), 2-phthalimidomethyl quinacridone (0.8 g) and polyethylene glycol 400 (360 g). Air was bubbled into the stirred mixture. The reaction mixture was heated with stirring and maintained at 90±2° C. for 3.0 hours. The dark blue reaction mixture was cooled to 25° C. To this mixture was added methanol (400 ml) with vigorous stirring.

Part A: One half of the above slurry was poured into water (900 ml). After ¼ hour of stirring the precipitated product was filtered, washed with hot (60° C.) water until the pH of the filtrate was 7.0. The resulting pigment presscake was dried overnight in an oven at 80° C. to yield 19.4 g of a deep magenta colored pigment with an X-ray diffraction of an extremely small particle size 2,9-dimethylquinacridone in an even lesser crystalline state than the pigment of Example 6, Part A.

Part B: The other half of the above slurry was poured into methanol (900 ml). After ¼ hour of stirring the precipitated product was filtered, washed with hot (60° C.) water until the pH of the filtrate was 7.0. The resulting pigment presscake was dried overnight in an oven at 80° C. to yield 19.4 g of a significantly smaller particle size 2,9-dimethylquinacridone of an attractively deep magenta color. The X-ray diffraction pattern showed a β polymorph having a lesser degree of crystallinity compared to the pigment of Example 6, Part B.

EXAMPLE 8

To a one liter four necked round bottomed flask equipped with a stirrer, thermometer, a gas inlet tube and reflux condenser was added aqueous sodium hydroxide (80 g; 50%), 2,9-dimethyl-6,13-dihydroquinacridone crude (58.8 g; 1.719 moles), anthraquinone-2-sulfonic acid (4.0 g), 2-phthalimidomethylquinacridone (1.2 g) and polyethylene glycol 400 (340 g). Air was bubbled into the stirred mixture. The reaction mixture was heated with stirring and maintained at 80±2° C. for 3.0 hours. The dark purple reaction mixture was cooled to 25° C. and poured in to methanol (1200 ml) with vigorous stirring. After ¼ hour of stirring the precipitated product was filtered, washed with methanol followed by hot (60° C.) water until the pH of the filtrate was 7.0. The resulting pigment presscake was dried overnight in an oven at 80° C. to yield 59.6 g of a very attractive deep magenta colored pigment exhibiting an X-ray diffraction pattern of a significantly smaller particle size pigment similar to the 2,9-dimethylquinacridone obtained in Example 7, Part B. Oxidations can be performed at a 15% pigment concentration/loading (even in the presence of a growth inhibitor) resulting in excellent pigments.

EXAMPLE 9

To a one liter four necked round bottomed flask equipped with a stirrer, thermometer, a gas inlet tube and reflux condenser was added aqueous sodium hydroxide (80 g; 50%), 2,9-dimethyl-6,13-dihydroquinacridone crude (60.0 g; 0.1754 moles), anthraquinone-2-sulfonic acid (4.0 g) and polyethylene glycol 400 (340 g). Air was bubbled into the stirred mixture. The reaction mixture was heated with stirring and maintained at 80±2° C. for 3.0 hours. The dark purple reaction mixture was cooled to 25° C. and poured in to methanol (1200 ml) with vigorous stirring. After ¼ hour of stirring the precipitated product was filtered, washed with methanol followed by hot (60° C.) water until the pH of the filtrate was 7.0. The resulting pigment presscake was dried overnight in an oven at 80° C. yield 59.8 g of a very attractive deep magenta colored pigment exhibiting an X-ray diffraction pattern of a significantly smaller particle size pigment similar to the 2,9-dimethylquinacridone obtained in Example 6, Part B. Oxidations can be performed at a 15% pigment concentration/loading providing excellent pigments.

EXAMPLE 10

To a one liter four necked round bottomed flask equipped with a stirrer, thermometer, a gas inlet tube and reflux condenser was added aqueous sodium hydroxide (80 g; 50%), 2,9-dimethyl-6,13-dihydroquinacridone crude (80.0 g; 2.339 moles), anthraquinone-2-sulfonic acid (4.0 g) and polyethylene glycol 400 (320 g). Air was bubbled into the stirred mixture. The reaction mixture was heated with stirring and maintained at 80±2° C. for 3.0 hours. The dark purple reaction mixture was cooled to 25° C. and poured in to methanol (1200 ml) with vigorous stirring. After ¼ hour of stirring the precipitated product was filtered, washed with methanol followed by hot (60° C.) water until the pH of the filtrate was 7.0. The resulting pigment presscake was dried overnight in an oven at 80° C. to yield 59.8 g of a very attractive deep magenta colored pigment exhibiting an X-ray diffraction pattern of a significantly smaller particle size pigment similar to the 2,9-dimethylquinacridone obtained in Example 6, Part B. Oxidations can be performed at a 20% pigment concentration/loading providing excellent pigments.

EXAMPLE 11

To a one liter four necked round bottomed flask equipped with a stirrer, thermometer, a gas inlet tube and reflux condenser was added aqueous sodium hydroxide (80 g; 50%), 2,9-dimethyl-6,13-dihydroquinacridone crude (60.0 g; 0.1754 moles), anthraquinone-2-sulfonic acid (4.0 g) and polyethylene glycol 200 (340 g). Air was bubbled into the stirred mixture. The reaction mixture was heated with stirring and maintained at 80±2° C. for 3.0 hours. The dark purple reaction mixture was cooled to 25° C. and poured in to methanol (1200 ml) with vigorous stirring. After ¼ hour of stirring the precipitated product was filtered, washed with methanol followed by hot (60° C.) water until the pH of the filtrate was 7.0. The resulting pigment presscake was dried overnight in an oven at 80° C. to yield 59.8 g of a magenta colored pigment exhibiting an X-ray diffraction pattern of a small particle size 2,9-dimethylquinacridone pigment containing an α and β mixed phase. Oxidation can be performed with PEG 200.

EXAMPLE 12

To a one liter four necked round bottomed flask equipped with a stirrer, thermometer, a gas inlet tube and reflux condenser was added aqueous sodium hydroxide (80 g; 50%), 2,9-dimethyl-6,13-dihydroquinacridone crude (60.0 g; 0.1754 moles), anthraquinone-2-sulfonic acid (4.0 g) and polyethylene glycol 300 (340 g). Air was bubbled in to the stirred mixture. The reaction mixture was heated with stirring and maintained at 80±2° C. for 3.0 hours. The dark purple reaction mixture was cooled to 25° C. and poured in to methanol (1200 ml) with vigorous stirring. After ¼ hour of stirring the precipitated product was filtered, washed with methanol followed by hot (60° C.) water until the pH of the filtrate was 7.0. The resulting pigment presscake was dried overnight in an oven at 80° C. to yield 59.8 g of a very attractive deep magenta colored pigment exhibiting an X-ray diffraction pattern of a significantly smaller particle size pigment similar to the 2,9-dimethylquinacridone obtained in Example 6, Part B. Oxidation performed in PEG 300 give excellent pigments.

EXAMPLE 13

To a one liter four necked round bottomed flask equipped with a stirrer, thermometer, a gas inlet tube and reflux condenser was added aqueous sodium hydroxide (40 g; 50%), 6,13-dihydroquinacridone crude (25.0 g; 0.0796 moles), anthraquinone-2-sulfonic acid (2.5 g), polyethylene glycol 400 (2.5 g) and N-methylpyrrolidin-2-one (200 g). Air was bubbled into the stirred mixture. The reaction mixture was heated with stirring and maintained at 90±2° C. for 3.0 hours. The deep violet-black reaction mixture was cooled to 70° C. To this mixture was added methanol (500 ml) with vigorous stirring. After ¼ hour of stirring the precipitated product was filtered, washed with methanol followed by hot (60° C.) water until the pH of the filtrate was 7.0. The resulting pigment presscake was dried overnight in an oven at 80° C. to yield 24.6 g of a dull violet colored pigment which analyzed for 96.6% quinacridone; 0.1% 6,13-dihydroquinacridone and 1.6% quinacridonequinone.

The infrared spectrum indicated a mixture of quinacridone and quinacridonequinone. The product showed an X-ray diffraction pattern of a β phase quinacridone. Catalytic amounts of polyethylene glycol 400 (with N-methylpyrrolidin-2-one) are shown to improve the purity of the quinacridone resulting from the oxidation of dihydroquinacridone.

EXAMPLE 14

To a one liter four necked round bottomed flask equipped with a stirrer, thermometer, a gas inlet tube and reflux condenser were added aqueous potassium hydroxide (44.5 g; 45%), 6,13-dihydroquinacridone crude (25.0 g; 0.0796 moles), anthraquinone-2-sulfonic acid (2.5 g), polyethylene glycol 400 (2.5 g) and N-methylpyrrolidin-2-one (200 g). Air was bubbled into the stirred mixture. The reaction mixture was heated with stirring and maintained at 90±2° C. for 3.0 hours. The deep violet-black reaction mixture was cooled to 50° C. To this mixture was added methanol (500 ml) with vigorous stirring. After ¼ hour of stirring the precipitated product was filtered, washed with methanol followed by hot (60° C.) water until the pH of the filtrate was 7.0. The resulting pigment presscake was dried at 80° C. in an oven overnight to yield 24.6 g of a dull violet colored pigment which analyzed for 97.3% quinacridone; 0.1% 6,13-dihydroquinacridone and 1.0% quinacridonequinone.

The product showed an X-ray diffraction pattern of a β phase quinacridone. Polyethylene glycol catalyzed oxidation of dihydroquinacridone using potassium hydroxide instead of sodium hydroxide in N-methylpyrrolidin-2-one yields quinacridone of high purity.

The foregoing examples are not limiting and numerous variations of the above-described specific embodiments can be made without departing from the spirit of the invention which is intended to be limited only by the language of the appended claims.

Comparative Example 1

To a one liter four necked round bottomed flask equipped with a stirrer, thermometer, a gas inlet tube and reflux condenser was added aqueous sodium hydroxide (80 g; 50%), 2,9-dimethyl-6,13-dihydroquinacridone crude (40.0 g; 0.117 moles), anthraquinone-2-sulfonic acid (4.0 g), 2-phthalimidomethylquinacridone (0.8 g) and ethylene glycol (360 g). Air was bubbled into the stirred mixture. The reaction mixture was heated with stirring and maintained at 90±2° C. for 0.5 hours. No reaction was observed. The reaction mixture stayed light pink. Essentially 2,9-dimethyl-6,13-dihydroquinacridone was recovered.

While polyalkylene glycols are particularly useful their monomeric ethylene glycol failed to oxidize the dihydroquinacridone.

Comparative Example 2

To a one liter four necked round bottomed flask equipped with a stirrer, thermometer, a gas inlet tube and reflux condenser was added aqueous sodium hydroxide (40 g; 50%), 2,9-dimethyl-6,13-dihydroquinacridone crude (25.0 g; 0.0731 moles), anthraquinone-2-sulfonic acid (2.5 g) and N-methyl pyrrolidin-2-one (250 g). Air was bubbled into the stirred mixture. The reaction mixture was heated with stirring and maintained at 80±2° C. for 3.0 hours. The dark blue reaction mixture was cooled to 50° C. and poured in to chilled (10° C.) aqueous methanol (1200 ml; 50%) with vigorous stirring. After ¼ hour of stirring the precipitated product was filtered, washed with methanol followed by hot (60° C.) water until the pH of the filtrate was 7.0. The resulting pigment presscake was dried overnight in an oven at 80° C. to yield 24.5 g of a dull magenta colored pigment which analyzed for 52.5% 2,9-dimethylquinacridone; 3.9% 2,9-dimethyl-6,13-dihydroquinacridone and 8.1% 2,9-dimethylquinacridonequinone.

The infrared spectrum and the X-ray diffraction pattern indicated a mixture of the above compounds. The foregoing demonstrates that N-methylpyrrolidin-2-one does not serve as a useful solvent for the oxidation of dimethyldihydroquinacridone.

Comparative Example 3

To a one liter four necked round bottomed flask equipped with a stirrer, thermometer, a gas inlet tube and reflux condenser was added aqueous sodium hydroxide (40 g; 50%), 6,13-dihydroquinacridone crude (25.0 g; 0.0796 moles), anthraquinone-2-sulfonic acid (2.5 g) and N-methylpyrrolidin-2-one (200 g). Air was bubbled into the stirred mixture. The reaction mixture was heated with stirring and maintained at 90±2° C. for 3.0 hours. The deep violet-black reaction mixture was cooled to 50° C. To this mixture was added methanol (500 ml) with vigorous stirring. After ¼ hour of stirring the precipitated product was filtered, washed with methanol followed by hot (60° C.) water until the pH of the filtrate was 7.0. The resulting pigment presscake was dried overnight in an oven at 80° C. to yield 24.6 g of a dull violet colored β phase quinacridone pigment which analyzed for 94.7% quinacridone; 0.1% 6,13-dihydroquinacridone and 2.2% quinacridonequinone.

The purity is significantly lower than in instant example 13.

What is claimed is:

1. A process for preparing an unsubstitued or substituted quinacridone of formula

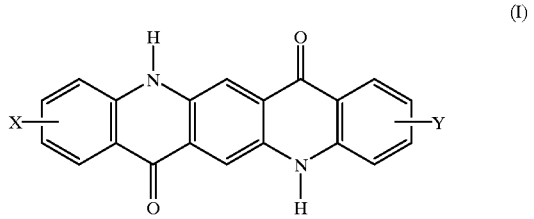

(I)

or a solid solution of quinacridones of formula (I), wherein X and Y in formula (I) are independently 1 or 2 substituents selected from hydrogen, fluorine, chlorine, $C_1$–$C_3$alkyl, $C_1$–$C_3$alkoxy and COOR wherein R is hydrogen or $C_1$–$C_{10}$alkyl, said process comprising:

a) oxidizing a salt of a corresponding 6,13-dihydroquinacridones of formula

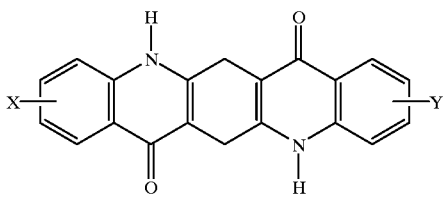 (II)

or salts of corresponding 6,13-dihydroquinacridones of formula II, with air or an oxygen containing gas mixture in a homogenous liquid reaction medium that consists essentially of an oxidative effective amount of a compound represented by formula

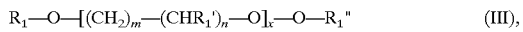 (III), wherein $R_1$, $R_1'$, $R_1''$ are, independently of one another, hydrogen or $C_1$–$C_4$alkyl, or $R_1$ and $R_1''$ are together $C_2$–$C_4$alkylene, m and n are 1 to 4, and x is 3 to 1000, in the presence of an aqueous base and a catalyst, wherein the compound according to formula (III) is present in an amount of at least 2 parts by weight per part by weight of the dihydroquinacridone or salt thereof to form an unsubstituted or substituted quinacridone that is dissolved in said reaction medium;

b) precipitation said dissolved unsubstituted or substituted quinacridone or the mixture of quinacridones from the reaction mixture of step a; and c) recovering said unsubstituted or substituted quinacridone or a solid solution of two or more quinacridones.

2. The process of claim 1, wherein said unsubstituted or substituted quinacridone is selected from the group consisting of unsubstituted quinacridone, 2,9-dichloroquinacridone, 2,9-difluoroquinacridone, 4,11-dichloroquinacridone, 4,11-difluoroquinacridone, 2,9-dicarboxyquinacridone, 3,10-dichloroquinacridone, 2,9-dimethylquinacridone, 4,11-dimethylquinacridone and 2,9-dimethoxyquinacridone.

3. The process according to claim 1, wherein the salt of a corresponding 6,13-dihydroquinacridone or a mixture of corresponding 6,13-dihydroquinacridones of formula II is oxidized with air or another oxygen containing gas mixture in a polyalkylene glycol medium in the presence of an aqueous base and a catalyst.

4. The process according to claim 3, wherein said polyalkylene glycol has a weight average molecular weight of from about 200 to about 600.

5. The process according to claim 3, wherein said polyalkylene glycol is present in an amount from about 25 to about 3 times the weight of 6,13-dihydroquinacridone.

6. The process according to claim 1, wherein said aqueous base is an aqueous solution of an alkali metal hydroxide.

7. The process according to claim 1, wherein a molar ratio of said base to said 6,13-dihydroquinacridone is from about 1:3 to about 1:39.

8. The process according to claim 1, wherein said oxygen-containing gas is air and said oxidation catalyst is an anthraquinone or a derivative thereof present in an amount of from about 0.005 to about 0.25 times the weight of 6,13-dihydroquinacridone.

9. The process according to claim 1, wherein oxidation is conducted at a temperature below 150° C.

10. The process according to claim 1, wherein said unsubstituted or substituted quinacridone is precipitated from said reaction mixture by drowning said reaction mixture into water, an alcohol or a mixture thereof or adding to said reaction mixture water, an alcohol or a mixture thereof.

11. The process according to claim 1, wherein reaction mixture is drowned into methanol, ethanol, n-propanol, iso-propanol, or n-butanol or an isomer thereof.

12. the process according to claim 1, wherein said unsubstituted or substituted quinacridone is precipitated from said reaction mixture by drowning said reaction into, or adding to said reaction mixture at least one mineral acid; an organic acid; or a mixture thereof.

13. The process according to claim 1, wherein said unsubstituted or substituted quinacridone is precipitated from said reaction mixture by introducing hydrogen chlorine gas into said reaction mixture.

14. The process according to claim 1, wherein a solid solution is prepared.

15. A process according to claim 14, wherein step a) is started separately in a different reactor for each salt of 6,13-dihydroquinacridone of formula II to form a reaction mixture, and the reaction mixtures are then a combined before said precipitating step b).

16. The process according to claim 7, wherein the molar ratio of said base to said 6,13-dihydroquinacridone is from about 1:4 to about 1:15.

17. The process according to claim 8, wherein said oxidation catalyst is selected from monochloroanthraquinone, dichloroanthraquinone, anthraquinone-2-sulfonic acid, anthraquinone-2,6-disulfonic acid and mixtures thereof.

18. The process according to claim 9, wherein said oxidation is conducted at a temperature from 50 to 100° C.

19. The process according to claim 9, wherein said oxidation is conducted at a temperature from 70 to 90° C.

20. The process according to claim 12, wherein said unsubstituted or substituted quinacridone is precipitated from said reaction mixture by drowning said reaction into, or adding to said reaction mixture at least one acid selected from hydrochloric acid, sulfuric acid, phosphoric acid, acetic acid or mixtures thereof.

* * * * *